(12) United States Patent
Vazhaeparambil et al.

(10) Patent No.: US 9,891,177 B2
(45) Date of Patent: Feb. 13, 2018

(54) TDI SENSOR IN A DARKFIELD SYSTEM

(71) Applicant: KLA-Tencor Corporation, Milpitas, CA (US)

(72) Inventors: Jijen Vazhaeparambil, Saratoga, CA (US); Guoheng Zhao, Palo Alto, CA (US); Daniel Kavaldjiev, San Jose, CA (US); Anatoly Romanovsky, Palo Alto, CA (US); Ivan Maleev, Pleasanton, CA (US); Christian Wolters, San Jose, CA (US); Stephen Biellak, Sunnyvale, CA (US); Bret Whiteside, Gilroy, CA (US); Donald Pettibone, San Jose, CA (US); Yung-Ho Alex Chuang, Cupertino, CA (US); David W. Shortt, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 375 days.

(21) Appl. No.: 14/506,321

(22) Filed: Oct. 3, 2014

(65) Prior Publication Data

US 2016/0097727 A1 Apr. 7, 2016

(51) Int. Cl.
*G01N 21/88* (2006.01)
*G01N 21/95* (2006.01)
*G06T 7/00* (2017.01)
*G01N 21/956* (2006.01)

(52) U.S. Cl.
CPC ..... *G01N 21/8851* (2013.01); *G01N 21/9501* (2013.01); *G01N 21/956* (2013.01); *G06T 7/0004* (2013.01); *G01N 2021/8887* (2013.01); *G01N 2021/8896* (2013.01); *G01N 2201/06113* (2013.01); *G01N 2201/103* (2013.01); *G01N 2201/12* (2013.01); *G06T 2207/10004* (2013.01); *G06T 2207/30148* (2013.01)

(58) Field of Classification Search
CPC ............. G01N 21/8851; G01N 21/956; G01N 21/9501
See application file for complete search history.

(56) References Cited

U.S. PATENT DOCUMENTS

| 6,288,780 | B1 | 9/2001 | Fairley et al. |
|---|---|---|---|
| 6,608,676 | B1 | 8/2003 | Zhao et al. |
| 7,227,984 | B2 | 6/2007 | Cavan |
| 7,525,694 | B2 | 4/2009 | Nishida |
| 7,609,309 | B2 | 10/2009 | Brown et al. |
| 7,952,633 | B2 | 5/2011 | Brown et al. |

(Continued)

OTHER PUBLICATIONS

PCT Search Report for PCT/US2015/053824 dated Dec. 28, 2015, 3 pages.

*Primary Examiner* — Kara E Geisel
*Assistant Examiner* — Amanda Merlino
(74) *Attorney, Agent, or Firm* — Suiter Swantz pc llo

(57) ABSTRACT

A wafer scanning system includes imaging collection optics to reduce the effective spot size. Smaller spot size decreases the number of photons scattered by the surface proportionally to the area of the spot. Air scatter is also reduced. TDI is used to produce a wafer image based on a plurality of image signals integrated over the direction of linear motion of the wafer. An illumination system floods the wafer with light, and the task of creating the spot is allocated to the imaging collection optics.

41 Claims, 5 Drawing Sheets

(56) References Cited

U.S. PATENT DOCUMENTS

| | | | |
|---|---|---|---|
| 8,004,666 B2* | 8/2011 | Shibata | G01N 21/21 356/237.1 |
| 8,624,971 B2 | 1/2014 | Brown et al. | |
| 8,692,916 B2* | 4/2014 | Lazovsky | H04N 5/347 348/296 |
| 8,772,731 B2 | 7/2014 | Subrahmanyan et al. | |
| 2004/0175028 A1 | 9/2004 | Cavan | |
| 2006/0103725 A1 | 5/2006 | Brown et al. | |
| 2007/0064135 A1 | 3/2007 | Brown et al. | |
| 2008/0079830 A1 | 4/2008 | LePage | |
| 2010/0188655 A1 | 7/2010 | Brown et al. | |
| 2012/0230602 A9 | 9/2012 | Goodnough et al. | |
| 2013/0016346 A1 | 1/2013 | Romanovsky et al. | |
| 2013/0270444 A1 | 10/2013 | Subrahmanyan et al. | |
| 2014/0043463 A1 | 2/2014 | Brown et al. | |
| 2014/0104468 A1 | 4/2014 | Parker et al. | |
| 2014/0158864 A1 | 6/2014 | Brown et al. | |

* cited by examiner

TDI SENSOR IN A DARKFIELD SYSTEM

FIELD OF THE INVENTION

The present invention is directed generally toward inspection systems for semiconductor wafers and more particularly toward inspection systems with time delay integration (TDI) sensors.

BACKGROUND OF THE INVENTION

Time delay integration (TDI) is an imaging process that produces a continuous image of a moving two-dimensional object. In a TDI system, image photons are converted to photocharges in an array of pixels. As the object is moved, the photocharges are shifted from pixel to pixel down the sensor, parallel to the axis of movement. By synchronizing the photocharge shift rate with the velocity of the object, the TDI can integrate signal intensity at a fixed position on the moving object to generate the image. The total integration time can be regulated by changing the speed of the image motion and providing more/less pixels in the direction of the movement.

TDI inspection systems can be used for inspecting wafers, masks, and/or reticles. A conventional TDI sensor includes a large array of photo sensor elements (charge-coupled devices (CCDs)) formed as a grid. For example, a conventional TDI sensor could be formed in a 1024×128 array of photo sensor elements. To achieve higher sensitivity than can be provided by using a conventional TDI sensor a plurality of TDI pixels can be arranged in a sub-pixel offset pattern. Sensor interleaving can advantageously increase the resolution and the anti-aliasing capability of a TDI inspection system.

At increasingly smaller technology nodes, it is desirable for the image to be significantly magnified at high resolution, thereby facilitating defect detection. At the same time, faster inspections are being requested, despite the increasing complexity of the wafers/masks/reticles being inspected. To accomplish these goals, the size of the TDI sensor arrays has increased.

Emerging semiconductor fabrication processes demand sensitivity to smaller and smaller particles. Current tools operate on the principle of detecting photons, scattered by defects such as aberrant particles, and differentiating "defect" photons from noise. Noise sources include "noise" photons, scattered by the wafer surface and air, and hardware noise, added to the signal by sensors and electronics. The more photons that are scattered by the defect, and the less noise, the easier it is to detect a defect.

However, the number of photons, scattered by a spherical particle, is proportional to the 6-th power of its diameter. With the same illumination, a 12 nm particle scatters approximately sixty-four times fewer photons than a 24 nm particle. Increasing the number of illumination photons is not an option because of the thermal damage threshold, above which the illumination photons begin to damage the surface.

Existing spot scanning technologies have reached the limit of inspection sensitivity. Technologies in patterned applications have specific implementation details and technology limitations such as available laser power, optical efficiencies, noise sources and XY stage specific implementations that limit inspection speed required for patterned and unpatterned applications.

Consequently, it would be advantageous if an apparatus existed that is suitable for very high resolution, real-time, darkfield wafer and reticle inspection.

SUMMARY OF THE INVENTION

Accordingly, the present invention is directed to a novel method and apparatus for very high resolution, real-time, darkfield wafer and reticle inspection.

In at least one embodiment of the present invention, a wafer scanning system includes imaging collection optics to collect scattered light. Imaging the illuminated wafer area onto a multi-pixel sensor results in each pixel receiving a fraction of the background signal, while the defect signal is imaged onto a much smaller number of pixels, increasing signal/background and signal/noise ratios for those pixels. Smaller spot size decreases the number of photons scattered by the surface proportionally to the area of the spot. Air scatter is also reduced. TDI is used to produce a wafer image based on a plurality of image signals integrated over the direction of linear motion of the wafer.

In at least one embodiment of the present invention, the illumination system floods the wafer with light, and the task of creating the spot is allocated to the imaging collection optics.

It is to be understood that both the foregoing general description and the following detailed description are exemplary and explanatory only and are not restrictive of the invention claimed. The accompanying drawings, which are incorporated in and constitute a part of the specification, illustrate an embodiment of the invention and together with the general description, serve to explain the principles.

BRIEF DESCRIPTION OF THE DRAWINGS

The numerous advantages of the present invention may be better understood by those skilled in the art by reference to the accompanying figures in which.

DETAILED DESCRIPTION OF THE INVENTION

Reference will now be made in detail to the subject matter disclosed, which is illustrated in the accompanying drawings. The scope of the invention is limited only by the claims; numerous alternatives, modifications and equivalents are encompassed. For the purpose of clarity, technical material that is known in the technical fields related to the embodiments has not been described in detail to avoid unnecessarily obscuring the description.

The process of time delay integration (TDI) and associated hardware are more fully described in U.S. Pat. Nos. 8,772,731; 8,624,971; 7,952,633; 7,609,309 and 7,227,984. Such processes and hardware are further described in U.S.

Pat. App. Pub. No. 20140158864; U.S. Patent App. Pub. No. 20140043463; U.S. Patent App. Pub. No. 20130270444; U.S. Patent App. Pub. No. 20100188655; U.S. Patent App. Pub. No. 20060103725; U.S. Patent App. Pub. No. 20130016346 and U.S. Patent App. Pub. No. 20040175028. All U.S. Patents and published U.S. Patent Applications are hereby incorporated by reference in their entirety.

Embodiments of the present invention may allow for narrow field TDI image acquisition. In the context of the present invention, a narrow field should be understood as a field aspect ratio sufficient to reduce blur. A TDI sensor according to embodiments of the present invention may be configured to receive narrow channel image streams and integrate the resulting time-delayed images into a single wafer image.

Embodiments of the present invention may include imaging collection optics having a high numerical aperture for collecting scattered photons from an illuminated, unpatterned wafer on the R-theta stage. Collecting scattered photons allows for darkfield defect detection.

Figure 1:
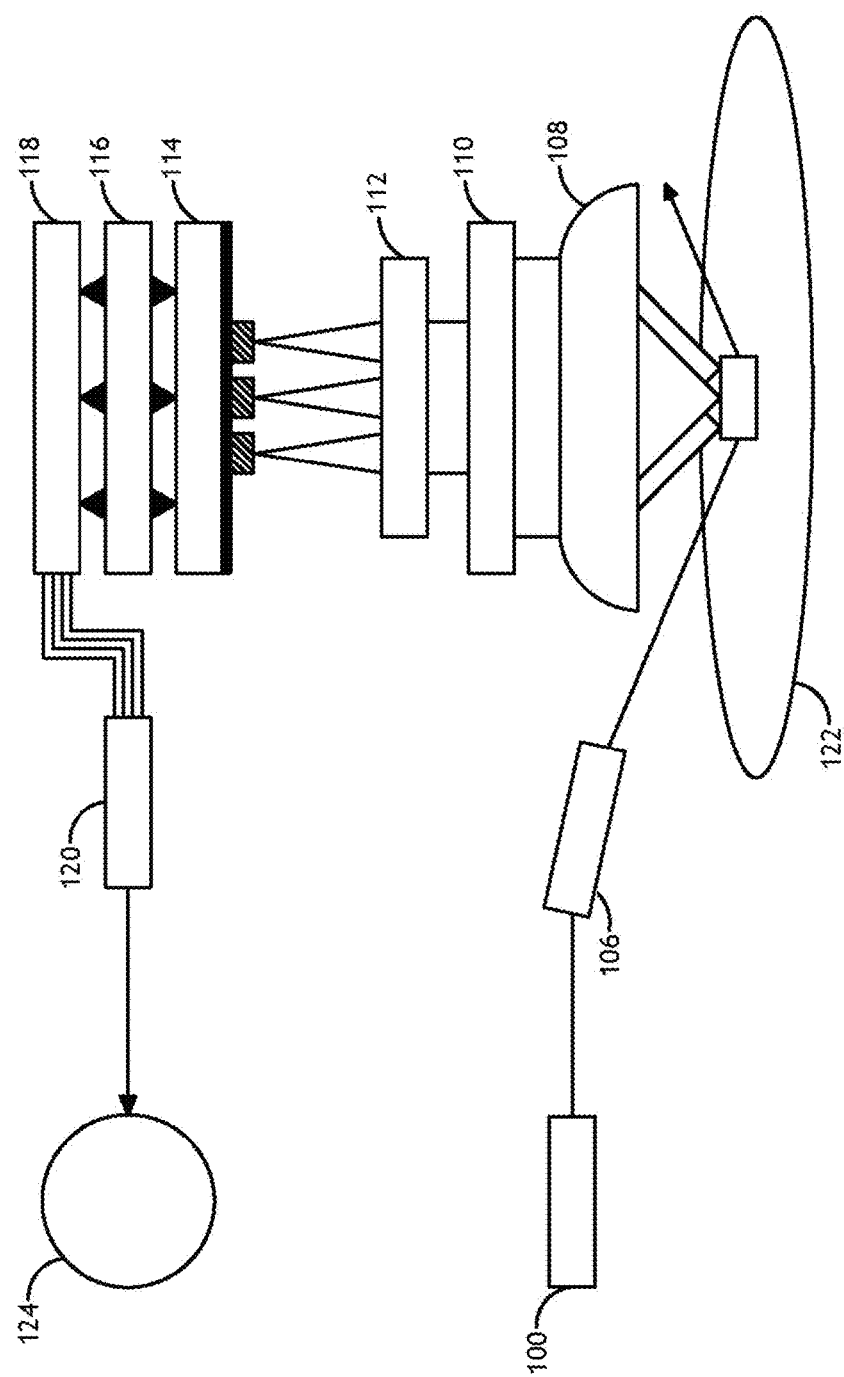
FIG. 1 shows a block diagram of a wafer inspection system according to one embodiment of the present invention.

Referring to FIG. 1, a block diagram of a wafer inspection system according to one embodiment of the present invention is shown. A wafer inspection system according to the present invention includes at least one illumination source 100 such as a laser. In one embodiment, the illumination source 100 may include a two to fifty Watt mode-locked laser operating between approximately 157 nm to 532 nm. The illumination source 100 may produce light configured to illuminate a wafer 122 at a desirable angle to ensure reflected light is not collected by a system of imaging collection optics 108. To facilitate a desired illumination pattern, the light may be transitioned through one or more optical elements such as, but not limited to, one or more lenses, one or more filters and one or more optical elements 106. In one embodiment, the illumination source 100 is configured to illuminate a narrow field portion of a moving wafer 122. It is noted that the Illumination may include any illumination profile known in the art. For example, the illumination may include, but is not limited to, a flat-top illumination profile (e.g., in one or two dimensions), a Gaussian illumination profile, a super-Gaussian illumination profile or any other suitable illumination profile.

Scattered light from the wafer 122 may be collected by a system of imaging collection optics 108 configured to direct the collected light into an afocal lens system 110. In one embodiment of the present invention, imaging collection optics 108 resolve a spot. In order to take advantage of the imaging collection optics 108, embodiments of the present invention may include a TDI CCD sensor with multiple pixels creating highly parallelized acquisition system instead of a single channel photomultiplier tube (PMT) or other single channel detector.

It is noted that in high quality optical systems the resolution is close to the diffraction limit. For example, the resolution may be less than 0.2 µm for 266 nm wavelength light. It is recognized, however that an actual resolution of approximately 0.5 µm is acceptable and represents a substantial improvement over spot scanning technology. In one embodiment, the case of a spot scanning system, the illumination spot may include oblique illumination, elongated by an angle of incidence (1/cos). For instance, in the case of 70° angle of incidence, the elongation factor is 2.92; that is to say the oblique illumination spot is inherently 2.92 times larger than normal along the direction of incident plane, which allows for resolution not much greater than 1 µm.

In another embodiment, the illumination spot may include normally incident laser illumination, impinging the surface of the wafer 122 at an angle that is substantially perpendicular to the surface of a wafer 122. It is noted herein that the utilization of oblique incident illumination in the inspection of a wafer is described generally in U.S. Patent App. Pub. No. 20130016346, which is incorporated previously herein by reference in the entirety.

In another embodiment, a collection lens mask system 112 may divide the focused light into a plurality of channels for delivery to a TDI element 118. The collection lens mask system 112 may include beam splitters for up to five channels. For example, the collection lens mask system 112 may include three channels. Light sensing may be enhanced by an intensifier 114 or electron-bombarded device at the collection lens mask system 112.

It is noted herein that TDI data acquisition allows for the use of continuous wave or quasi-continuous wave lasers at high power and controlled illumination intensity. The selection of the TDI width includes a trade-off between geometrical blur caused by the R-Theta stage motion and illumination intensity. In another embodiment, an adjustment of the TDI clock may be used to continuously vary inspection in a single optical configuration.

In one embodiment, a tophat profile may be obtained by using an optical element 106. In another embodiment, a tophat profile may be obtained with two or more narrow long Gaussian spots that are separated slightly in a tangential axis, but overlap at about half the spot size in the radial axis. In this regard, the summed intensity, carried out by TDI integration, results in a nearly tophat profile.

Furthermore, additional embodiments of the present invention may include multiple spot illumination. It is noted herein that multiple spot illumination may be carried out in any manner known in the art. For example, multiple spot, or "multi-patch," illumination used in the inspection of a wafer is described in detail in U.S. Patent App. Pub. No. 20130016346, which is incorporated previously herein by reference in the entirety.

In another embodiment, the collection lens mask system 112 may deliver the one or more channels of focused, split light to an intensifier 114 or a sensor relay 116. In one embodiment, the intensifier 114 is switchable, and can be moved out of the optical path and replaced by the sensor relay 116 so that the intensifier 114 is only used for low light layers. In another embodiment, in the case of bright layers, such as very rough films, images are directly relayed to the TDI element 118, so that intensifier 114 life time can be extended and additional blur of the intensifier 114 can be avoided.

It is noted herein that the intensifier 114 and a sensor relay 116 may provide optical gain of, for example, 5-50 photon/photon. Further, light sensing by a TDI element 118 after the intensifier 114 may have a quantum efficiency in the range of 0.2-1.0. In one embodiment, the TDI element 118 is configured for receiving one or more channel optical streams. In one embodiment, a first stream may have an optical resolution that is sampled by a single pixel or a limited number of pixels of the TDI element 118. In another embodiment, a second stream may have an optical resolution that is sampled by a single pixel or limited number of pixels of the TDI element 118. In another embodiment, the first stream and second stream may have different optical resolutions that are sampled by different number of pixels of the TDI element 118. The TDI element 118 may include, but is not limited to, a single TDI chip, separate TDI chips, or independent TDI cameras receiving different streams. In another embodiment, the first stream and second stream may have the same optical resolution.

In one embodiment, signals from the TDI element 118 may be sent to an image processing computer 120 to produce multiple wafer images 124 from the separate streams of signals. In another embodiment, the image processing computer 120 may produce a wafer image 124 based on the data stream from the detector. In some embodiments, for example, anywhere from 10 to 10000 pixels may be utilized, and line rates of anywhere from 100 kHz-100 Mhz, or any line rate that achieves the desired wafer throughput, may be utilized. It is noted herein that the above values and ranges are provided merely for illustrative purposes and should not be interpreted as a limitation on the present invention.

In another embodiment, in the case of high sensitivity scans, the linear speed of the rotation of wafer 122 can reach approximately 0.1 m/s. In another embodiment, the linear speed associated with the rotation of the wafer 122 may reach 100 m/s, in the case of high throughput scans for certain radii of the wafer 122. For example, linear speeds from <0.1 m/s to >100 m/s are envisioned. It is noted herein that the above linear speed range is provided merely for illustrative purposes and should not be interpreted as a limitation on the present invention.

While much of the present disclosure has focused on the inspection of unpatterned wafers, it is recognized herein that the principles and various embodiments of the present invention may be extended to the inspection of patterned wafers. The inspection of unpatterned wafers is described in detail in U.S. Patent App. Pub. No. 20130016346, which is incorporated previously herein by reference in the entirety.

While elements having certain properties or ranges of properties are described, a person skilled in the art may appreciate that many variations of wavelength, scanning optics and elements of various optical properties are conceived. For example, in the case of the TDI element 118, the pixels may be binned in the integration direction for higher throughput. By way of another example, in the case of the TDI element 118, a readout clock may be set to different frequencies to accommodate linear speed variation along the radius of spiral scan.

Figure 2A:
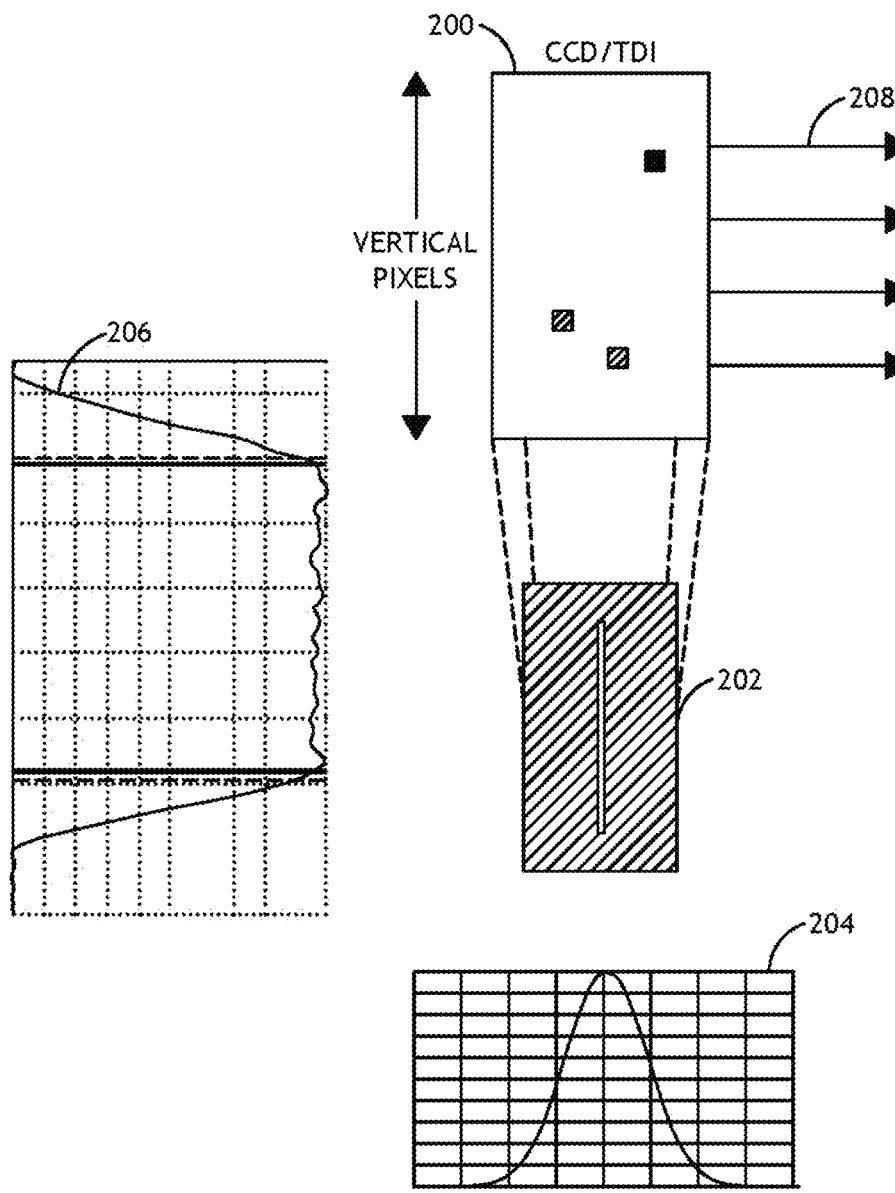
FIG. 2A shows a graphical representation of a TDI device and corresponding signal patterns.

Referring to FIG. 2A, a graphical representation of a TDI CCD and corresponding signal patterns is shown. For instance, a TDI 200 configured for TDI scans of an illuminated portion of a wafer 202 is shown. For example, in a system having an illumination source that illuminates a wafer at a selected angle (as shown in FIG. 1), the TDI 200 may be oriented such that the vertical axis of the TDI 200 coincides with the radial direction of R-theta scanning and the horizontal axis, which is the TDI readout direction 208 of the TDI 200 that coincides with the tangential direction of r-theta scanning. In one embodiment, the illumination profile associated with the light intensity 206 along the radial axis includes a top-hat profile for achieving a uniform sensitivity and light intensity 204 along the tangential axis. It is further noted that the illumination profile associated with light intensity 206 may include any illumination profile known in the art suitable providing an energy profile confined to a narrow width, such as, but not limited to, a Gaussian profile and the like. As the wafer 202 moves, the time delay integration of signals from the TDI 200 is synchronized such that charge is transferred at the same linear speed as the moving wafer 202. In one embodiment, the TDI 200 may include approximately 1024 vertical pixels and 128 horizontal pixels. It is noted herein that the above that the number of pixels of the charged-coupled device is provided merely for illustrative purposes and should not be interpreted as a limitation on the present invention.

Figure 2B:
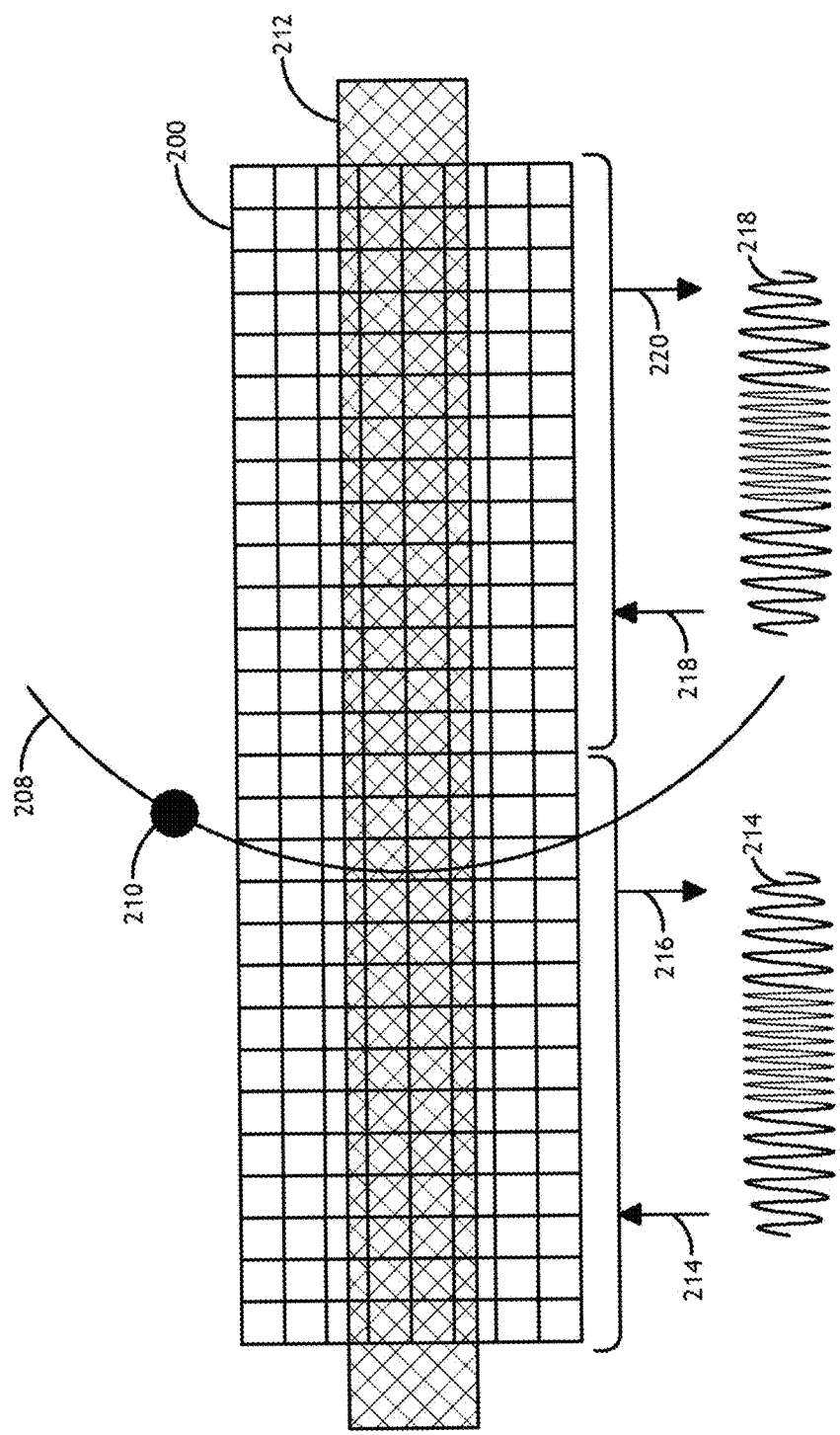
FIG. 2B shows a graphical representation of a TDI device and illumination pattern of a wafer.

Referring to FIG. 2B, a graphical representation of a TDI and illumination pattern of a wafer is shown. In one embodiment, a TDI sensor 200 scans a rotating wafer. In another embodiment, the direction of rotation, coupled with the length of the TDI sensor 200, produces a disparity in the linear speed of the wafer relative to different portions of the TDI sensor 200. For example, the rotating wafer may produce a slower linear speed across the narrow illumination field 212 in the portion of the TDI sensor 200 closest to the center of the wafer and a faster linear speed across the narrow illumination field 212 in the portion of the TDI sensor 200 closest to the edge of the wafer.

While the linear speed of the particle moving in the TDI integration direction varies depending on the relative position of the particle along the length of the TDI sensor 200, the speed of charge integration during time delay integration is generally constant across the entire field. The difference in linear speed as compared to charge integration speed results in image blur and defect signal degradation. In addition, the difference between the arc path of a point on a wafer and the straight line of charge integration during time delay integration also results in image blur. For xample, the blur caused by arc path 208 tends to be dominant.

In another embodiment, the blur is measured against the pixel size or the optical resolution of the imaging system, which is preferably less than a fraction of the optical resolution. In another embodiment, the blur can be minimized with a narrow illumination field 212, which serves to combine the high light efficiency of TDI sensors 200 and the high speed of R-theta scanning to achieve high sensitivity and high speed wafer inspection. In another embodiment, an imaging system may compensate for loss of sensitivity caused by image blur with longer integration time towards the center of wafer where linear speed is lower and blur is stronger due to small radius of rotation.

In one embodiment, the TDI sensor 200 includes multiple readout elements 216, 220, also referred to herein as "taps." In one embodiment, each of the readout elements 216, 220 corresponds to a separate portion of the TDI sensor 200. In another embodiment, each of the readout elements 216, 220, or portion of the TDI sensor 200 corresponding to each of the readout elements 216, 220, may be driven by a variable clock signal 214, 218. In one embodiment, each variable clock signal 214, 218 is configured to control readout signals to the readout elements 216, 220 as the linear speed of the TDI sensor 200 relative to the illumination field 212 varies due to the rotation of the wafer. In another embodiment, differences in linear speed due to the distance of disparate portions of the TDI sensor 200 may be accounted for with variances in a first clock signal 214 as compared to a second clock signal 218.

It is noted herein that the longer integration time towards the wafer center may result in wafer damage. As such, the intensity of the narrow illumination field 212 may be adjusted based on the distance of the TDI sensor 200 from the axis of rotation of the wafer to avoid wafer damage.

Figure 3:
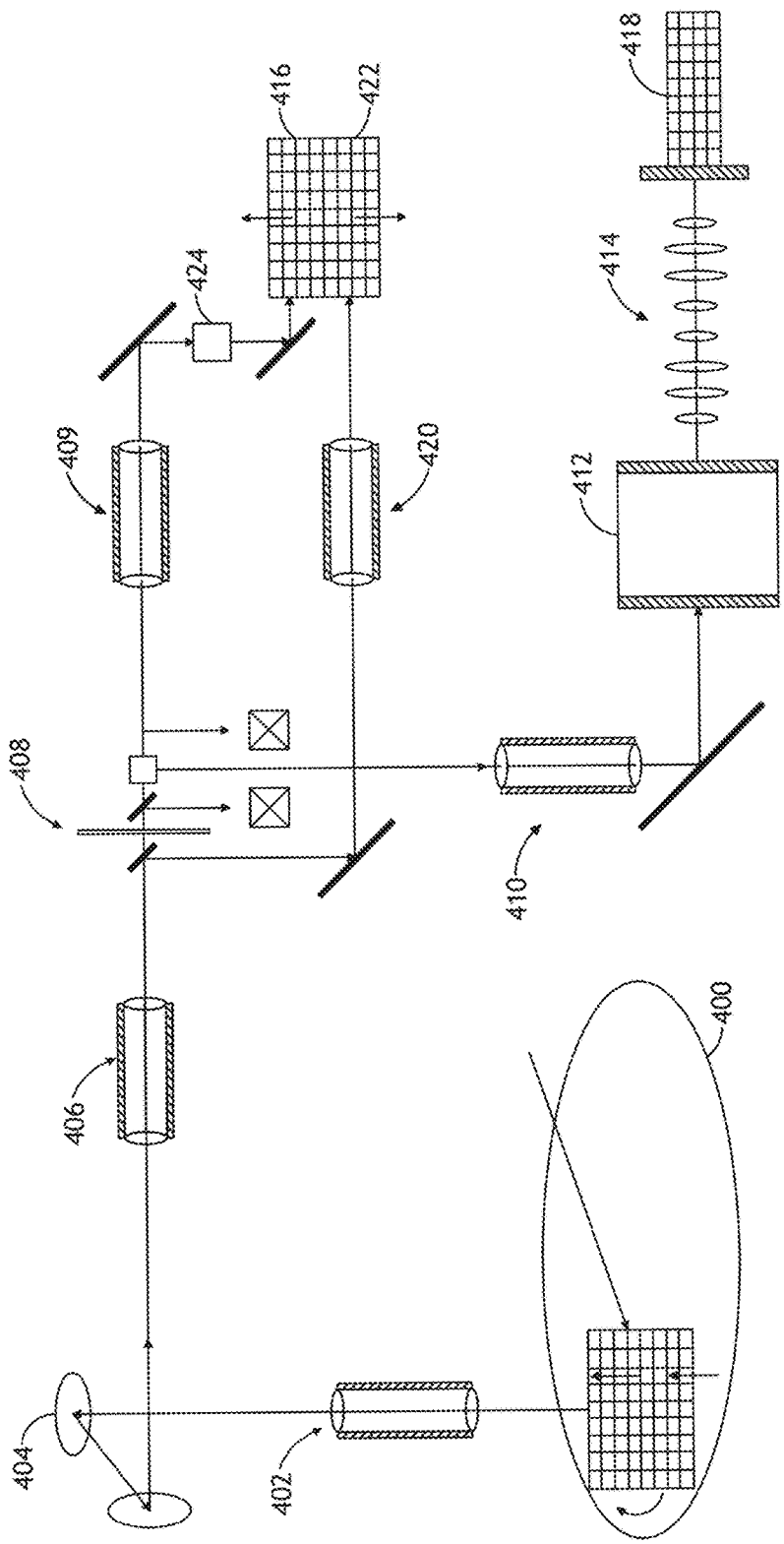
FIG. 3 shows a block diagram of a system for scanning a wafer according to one embodiment of the present invention.

Referring to FIG. 3, a block diagram of a system for scanning a wafer according to one embodiment of the present invention is shown. In one embodiment, a narrow long field on a wafer 400 is illuminated with a light source at a selected angle in a darkfield configuration such that only scattered photons are collected by a system of imaging collection optics 402. In another embodiment, illumination optics, associated with the light source, and collection optics 402 may include optical elements for controlling polarization. In another embodiment, the beam from the imaging collection optics 402 is then delivered to an afocal lens system 406. In another embodiment, the system of FIG. 3 may include any additional optical element or optical elements know in the art. For example, the system may include, but is not limited to a set of mirrors for directing the beam from the imaging collection optics 402 to additional portions of the system.

In one embodiment, the beam from the afocal lens system 406 may be directed to a Fourier plane beam splitter 408. In this regard, the Fourier plane beam splitter 408 may split the beam into a plurality of optical channels. In one embodiment, the Fourier plane beam splitter 408 includes a polarizing beam slipping cube and one or more masks.

In another embodiment, a first beam from a beam splitter 408 may be sent to a first lens system 409, which focuses the first beam on a first TDI camera 416. In another embodiment, the first beam may be transmitted through a beam inverting element 424 interposed between the first lens system 409 and the first charge-coupled device camera 416. In another embodiment, the first TDI camera 416 may be configured for a first magnification.

In another embodiment, a second beam from the beam splitter 408 may be sent to a second lens system 410 that focuses the second beam on a second TDI camera 418. In another embodiment, the second beam may be transmitted through a relay lens system 414. In another embodiment, an intensifier 412 may be interposed between the second lens system 410 and the relay lens system 414 to intensify an otherwise weak beam. In another embodiment, the second TDI camera 418 may be configured for a second magnification, different from the first magnification.

In another embodiment, a third beam from the beam splitter 408 may be sent to a third lens system 420 that focuses the third beam on a third TDI camera 422. In another embodiment, the first TDI camera 416 and the third TDI camera 422 may be one combined device, whereby the first beam and third beam are each focused on a portion of the combined device. For example, the first TDI camera 416 and the third TDI camera 422 may include a split readout utilizing both sides of a single TDI sensor. In such an embodiment, one side of the single TDI sensor moves with the wafer, while the signal moves in the opposite direction on the opposite side of the single TDI sensor.

In another embodiment, additional beams may originate from the beam splitter 408. For example, a fourth beam collected from another portion of the beam splitter 408 and a fifth beam collected from the same portion of one of the first, second, third or fourth beams but having a different polarization. In another embodiment, the fourth and fifth beams may utilize an existing coupled device camera 416, 418, 422, or may co-utilize a coupled device camera similar to the first beam and the third beam.

In another embodiment, signals from at least one of the coupled device cameras 416, 418, 422 may be utilized to produce a wafer image through TDI. In this regard, each coupled device camera 416, 418, 422 produces a signal corresponding to an illuminated field as the wafer moves over time.

Figure 4:
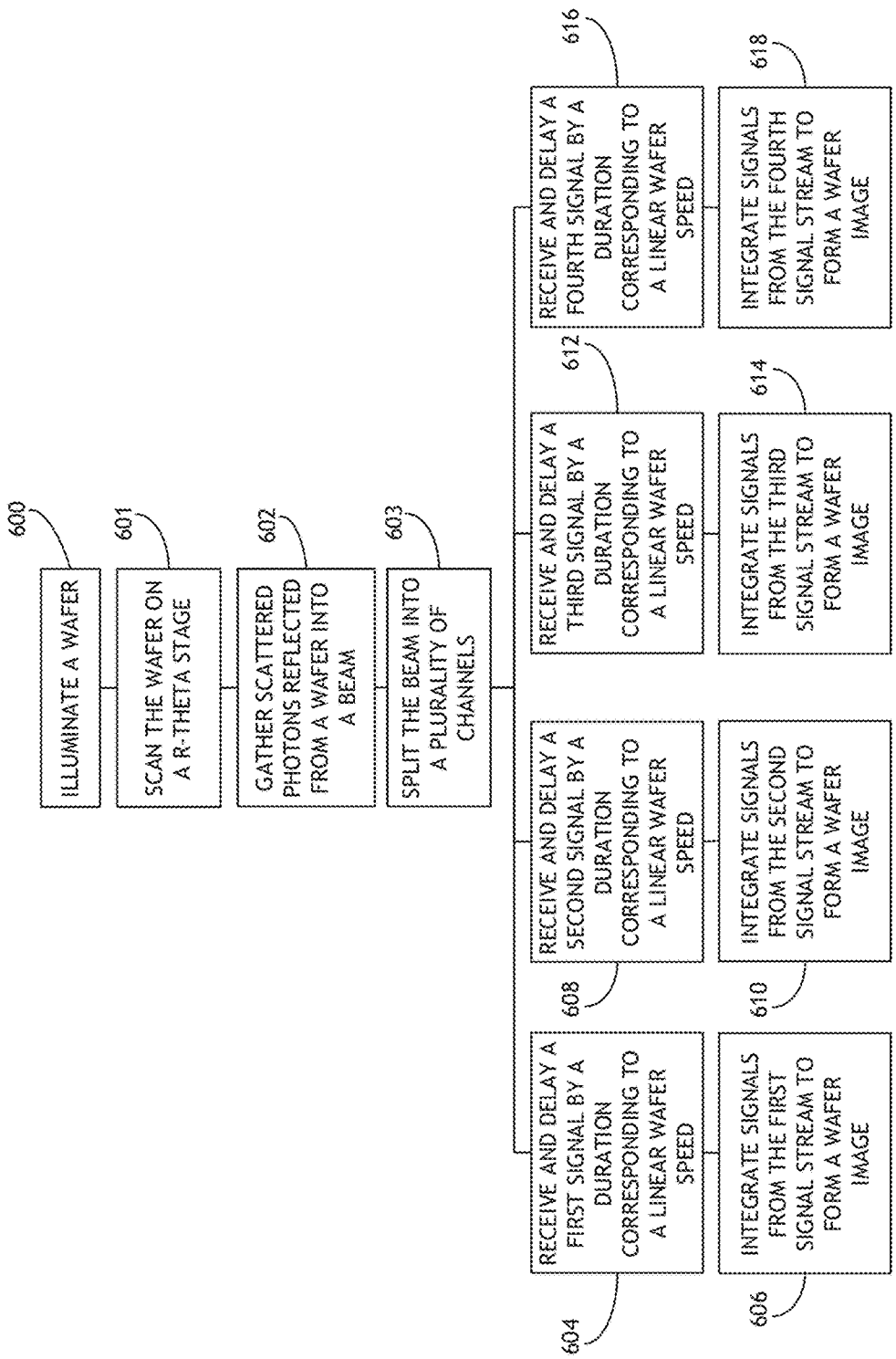
FIG. 4 shows a flowchart of a method for illuminating and inspecting semiconductor wafers according one embodiment of the present invention.

Referring to FIG. 4, a flowchart of a method for illuminating and inspecting semiconductor wafers according one embodiment of the present invention is shown. In one embodiment, a wafer is illuminated 600 with a long narrow illumination field. In another embodiment, the wafer is scanned 601 on an R-theta stage where an inspection system gathers 602 scattered photons from the moving wafer into a beam. In another embodiment, the beam is then split 603 into a plurality of channels. In another embodiment, a first beam is received and delayed 604 by a first time-delay integration charge coupled device, a second beam is received and delayed 608 by a second time-delay integration charge coupled device and a third beam is received and delayed 612 by a third time-delay integration charge coupled device.

In another embodiment, the signal from the first TDI may be delayed by a duration corresponding to the linear speed of the moving wafer. Likewise, the signal from the second TDI may be delayed by a duration corresponding to the linear speed of the moving wafer and the signal from the third time-delay integration charge-coupled device may be delayed by a duration corresponding to the linear speed of the moving wafer. In another embodiment, individual signals from each signal stream, or portions of individual signals may be adjusted, filtered or otherwise transformed to account for blur due to differences in linear speed across the based on varying distances of each TDI sensor pixel from the axis of rotation of the wafer. In another embodiment, signals from the first signal stream may be integrated 606 to form a first wafer image; signals from the second signal stream may be integrated 610 to form a second wafer image; and signals from the third signal stream may be integrated 614 to form a third wafer image. A person skilled in the art will appreciate that the present invention is not limited to three signal streams, and that the principles described herein are applicable to a system including N signal streams.

Furthermore, each signal stream may be analyzed by a processor to detect defects. Signal streams corresponding to scattered light collected from an illuminated wafer may be analyzed individually or with relation to one another, or by combining the signal streams for analysis.

It is believed that the present invention and many of its attendant advantages will be understood by the foregoing description of embodiments of the present invention, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A method for inspecting semiconductor wafers comprising:
   illuminating a moving wafer disposed on an R-Theta stage with an illumination field;
   collecting light from the moving wafer;
   receiving a first image stream from a time-delay integration sensor during rotational scanning and delaying the first image stream by a duration corresponding to a linear speed of the moving wafer; and
   integrating the first delayed image stream to produce a first wafer image,
   wherein:
      the time-delay integration sensor comprises one or more readout elements corresponding to a section of long dimension of the time-delay integration sensor, each of the one or more readout elements associated with a clock, a first readout element of the one or more readout elements associated with the first image stream; and
      a first clock signal associated with the first readout element is configured to reduce a blur caused by a linear speed disparity.

2. The method of claim 1, wherein:
   illuminating the moving wafer comprises illuminating the moving wafer at an angle; and collecting the light comprises excluding unscattered photons.

3. The method of claim 1, further comprising intensifying the first image stream wherein the first image stream requires high sensitivity.

4. The method of claim 1, further comprising:
splitting the collected light into a second image stream;
receiving the second image stream by a time-delay integration charge coupled device; and
integrating the second delayed image stream to produce a second wafer image,
wherein a second clock signal associated with the second image stream is configured to reduce a blur caused by a linear speed disparity.

5. The method of claim 4, further comprising intensifying at least one of the first image stream and the second image stream with either a discrete intensifier or an electron-bombarded device.

6. The method of claim 4, further comprising analyzing at least one of the first image stream and the second image stream to detect defects in the moving wafer.

7. The method of claim 4, wherein the first image stream and second image stream are received by separate portions of the same time-delay integration charge coupled device.

8. The method of claim 7, further comprising inverting the second image, wherein the first image stream corresponds to a first direction of wafer movement and the second image stream corresponds to an opposite direction.

9. The method of claim 1, further comprising adjusting an intensity of the narrow illumination field based on a distance of a TDI from an axis of rotation of the moving wafer.

10. The method of claim 1, wherein the first clock signal comprises a varying frequency corresponding to a linear speed disparity of a time-delay integration charge coupled device relative to the moving wafer during different portions of a rotation cycle.

11. The method of claim 1, wherein illuminating the moving wafer comprises generating a tophat illumination pattern by at least one of a diffractive optical element or two or more overlapped Gaussian spots.

12. The method of claim 1, wherein the illumination field comprises a flat-top profile.

13. The method of claim 1, wherein the illumination field comprises a Gaussian profile.

14. The method of claim 1, wherein the illumination field comprises a supergaussian profile.

15. The method of claim 1, wherein the moving wafer is unpatterned.

16. The method of claim 1, wherein the moving wafer is patterned.

17. An wafer inspection apparatus comprising:
an illumination system including an illumination source configured to illuminate a field of a moving wafer;
an image collection apparatus comprising one or more lenses configured to collect light from the moving wafer;
a beam splitter configured to split the collected light into a first image stream and a second image stream;
a first time-delay integration sensor configured to receive and delay the first image stream by a duration corresponding to a linear speed of the moving wafer, the time-delay integration sensor comprising at least one readout element associated with the first image stream, corresponding to a section of long dimension of the time-delay integration sensor, and associated with a clock configured to reduce a blur caused by a linear speed disparity;
a second time-delay integration sensor configured to receive and delay the second image stream by a duration corresponding to a linear speed of the moving wafer; and
an image processing computer configured to produce a first wafer image from the first delayed image stream and a second wafer image from the second delayed image stream.

18. The apparatus of claim 17, wherein the illumination system is configured to illuminate the moving wafer at an angle, and wherein the one or more lenses of the image collection apparatus are configured to exclude unscattered photons.

19. The apparatus of claim 18, wherein the illumination source of the illumination system comprises one or more lasers.

20. The Apparatus of claim 19, wherein each of the one or more lasers is configured to operate in different wavelengths.

21. The apparatus of claim 18, wherein the illumination system is configured to illuminate the moving wafer at an angle of between 60° and 85°.

22. The apparatus of claim 17, wherein the image collection apparatus comprises a refractive based collection system.

23. The apparatus of claim 17, wherein the image collection apparatus comprises a catadioptric based collection system.

24. The apparatus of claim 17, further comprising one or more intensifiers, each of the one or more intensifiers configured to intensify one or more of the first image stream and the second image stream.

25. The apparatus of claim 17, wherein the illumination system is configured to adjust an intensity of the narrow illumination field based on a distance of a TDI from an axis of rotation of the moving wafer.

26. The apparatus of claim 17, wherein the illumination system is configured to control the polarization of emitted light.

27. The apparatus of claim 17, wherein the image collection apparatus is configured to filter the collected light based on polarization.

28. The apparatus of claim 17, wherein the first time-delay integration sensor is associated with a first magnification.

29. The apparatus of claim 28, wherein the second time-delay integration sensor is associated with a second magnification.

30. The apparatus of claim 17, wherein the moving wafer is unpatterned.

31. The apparatus of claim 17, wherein the moving wafer is patterned.

32. A wafer imaging device comprising:
an illumination means for illuminating a moving wafer;
an image collection apparatus comprising one or more lenses configured to collect scattered light from the moving wafer;
a beam splitting means for splitting the collected scattered light into a first image stream and a second image stream;
a first time-delay imaging means for receiving and delaying the first image stream by a duration corresponding to a linear speed of the moving wafer, the time-delay integration sensor comprising at least one readout element associated with the first image stream, corresponding to a section of long dimension of the time-delay integration sensor, and associated with a clock configured to reduce a blur caused by a linear speed disparity;

a second time-delay imaging means for receiving and delaying the second image stream by a duration corresponding to a linear speed of the moving wafer; and an image processing means for producing a first wafer image base on the first delayed image stream and a second wafer image based on the second delayed image stream.

33. The device of claim 32, wherein:

the illumination means is configured for illuminating the moving wafer at an angle; and the image collection apparatus is configured to exclude unscattered photons.

34. The device of claim 32, further comprising an intensifying means for intensifying the first image stream.

35. The device of claim 32, wherein:

the beam splitting means is further configured to split the collected, scattered light into a third image stream;

the first time-delay imaging means is further configured for receiving and delaying the third image stream by a duration corresponding to a linear speed of the moving wafer; and the image processing means is further configured for producing a third image based on the third image stream.

36. The device of claim 35, further comprising a processing element configured to receive and analyze one or more of the first image stream, second image stream and third image stream to detect defects in the moving wafer.

37. The device of claim 35, wherein the beam splitter is further configured to split the collected, scattered light into a fourth image stream.

38. The device of claim 37, wherein the beam splitter is further configured to split the collected, scattered light into a fifth image stream.

39. The device of claim 38, wherein the beam splitter is further configured to split the collected, scattered light into a sixth image stream.

40. The device of claim 32, wherein the illumination means is configured to adjust an intensity of the narrow illumination field based on a distance of a TDI from an axis of rotation of the moving wafer.

41. A method for inspecting semiconductor wafers comprising:

illuminating a moving wafer disposed on an R-Theta stage with an illumination field;

collecting light from the moving wafer;

receiving a first image stream from a time-delay integration sensor during rotational scanning and delaying the first image stream by a duration corresponding to a linear speed of the moving wafer; and integrating the first delayed image stream to produce a first wafer image, wherein:

the time-delay integration sensor bins pixels along the direction of integration;

the time-delay integration sensor comprises one or more readout elements corresponding to a section of long dimension of the time-delay integration sensor, each of the one or more readout elements associated with a clock, a first readout element of the one or more readout elements associated with the first image stream; and a first clock signal associated with the first readout element is configured to reduce a blur caused by a linear speed disparity.

* * * * *